(12) United States Patent
Mickalonis

(10) Patent No.: US 11,369,152 B2
(45) Date of Patent: Jun. 28, 2022

(54) THERAPEUTIC GARMENTS AND METHODS OF USE THEREOF

(71) Applicant: Vanessa Mickalonis, Mechanicville, NY (US)

(72) Inventor: Vanessa Mickalonis, Mechanicville, NY (US)

(*) Notice: Subject to any disclaimer, the term of this patent is extended or adjusted under 35 U.S.C. 154(b) by 0 days.

(21) Appl. No.: 17/111,762

(22) Filed: Dec. 4, 2020

(65) Prior Publication Data

US 2021/0169155 A1    Jun. 10, 2021

Related U.S. Application Data

(60) Provisional application No. 62/943,323, filed on Dec. 4, 2019.

(51) Int. Cl.
| | | |
|---|---|---|
| *A41D 13/00* | (2006.01) | |
| *A61M 21/00* | (2006.01) | |
| *A41D 27/20* | (2006.01) | |
| *A61J 15/00* | (2006.01) | |

(52) U.S. Cl.
CPC ....... *A41D 13/0015* (2013.01); *A41D 27/208* (2013.01); *A61J 15/0011* (2013.01); *A61M 21/00* (2013.01); *A41D 2400/32* (2013.01); *A61M 2021/0016* (2013.01); *A61M 2205/05* (2013.01); *A61M 2209/088* (2013.01)

(58) Field of Classification Search
CPC ............ A41D 2400/32; A41D 2400/46; A41D 13/0015–0017; A41D 13/0058; A41D 13/02; A41D 2600/10; A61M 21/00–02
See application file for complete search history.

(56) References Cited

U.S. PATENT DOCUMENTS

| | | | |
|---|---|---|---|
| 5,476,492 A | 12/1995 | Unrug | |
| 7,112,343 B1 | 9/2006 | Shoemake | |
| 7,887,853 B1* | 2/2011 | Assaad | A61K 36/63 424/725 |
| 9,320,643 B2 | 4/2016 | Meneses | |
| 2002/0124294 A1* | 9/2002 | McKenzie | A41D 13/0002 2/69 |
| 2003/0131394 A1* | 7/2003 | Chou | A41D 13/0015 2/115 |
| 2005/0246813 A1* | 11/2005 | Davis | A41D 13/0056 2/69 |

(Continued)

FOREIGN PATENT DOCUMENTS

CN          105040472          11/2015

*Primary Examiner* — Thaddeus B Cox
(74) *Attorney, Agent, or Firm* — Bradley Arant Boult Cummings LLP

(57) ABSTRACT

The present invention relates to an apparatus that provides therapeutic effects and a source of hydration. The apparatus includes a garment that has one or more compartments for storing a therapeutic element. The therapeutic element may include one or more herbs, essential oils, and combinations thereof. The apparatus also includes a portable drinking apparatus attached to the garment. The portable drinking apparatus includes a pouch having a liquid reservoir inserted therein and a drinking tube having a first end in fluid communication with the liquid reservoir and a second end having a mouth operated valve. Methods of use are also disclosed.

12 Claims, 5 Drawing Sheets

(56) References Cited

U.S. PATENT DOCUMENTS

| | | | |
|---|---|---|---|
| 2007/0135777 A1* | 6/2007 | Greene | A61K 9/70 604/308 |
| 2016/0302501 A1* | 10/2016 | Peterson | A41D 27/20 |
| 2018/0028776 A1* | 2/2018 | Clark | B65D 65/02 |
| 2020/0197298 A1* | 6/2020 | Lindsay | A61K 9/007 |

* cited by examiner

THERAPEUTIC GARMENTS AND METHODS OF USE THEREOF

CROSS-REFERENCE TO RELATED APPLICATION

This application claims the benefit of and priority to U.S. Provisional Application No. 62/943,323, filed on Dec. 4, 2019, and entitled "Therapeutic Garments and Methods of Use Thereof," the disclosure of which is expressly incorporated by reference in its entirety.

FIELD OF THE INVENTION

The present invention relates generally to garments, and specifically to garments that provide therapeutic effects and a source of hydration.

BACKGROUND OF THE INVENTION

Herbs and essential oils have been used in aromatherapy applications at various times throughout history to restore and enhance health, beauty, and well-being. Aromatherapy has been known to have powerful physiological and psychological effects. The scents of herbs and essential oils stimulate the olfactory system and affect the limbic system, which is linked to emotions, heart rate, blood pressure, breathing, memory, stress, and hormone balance. These benefits are particularly advantageous for athletes who would like to enhance their athletic performance and recover more effectively and quickly after an intense workout. Accordingly, there is a need for a garment that can be worn during exercise and/or after exercise that provides immediate aromatherapeutic effects and increased hydration.

SUMMARY OF THE INVENTION

The problems described above, as well as others, are addressed by the following inventions, although it is to be understood that not every embodiment of the inventions described herein will address each of the problems described above.

In some embodiments, an apparatus for providing a dual therapy is provided. The apparatus for providing a dual therapy may include a garment including a torso portion and a pair of leg portions, wherein at least one of the torso portion and the leg portions include a compartment, wherein the compartment includes a therapeutic element selected from the group consisting of an herb, an essential oil, and combinations thereof, and a portable drinking apparatus operatively attached to the garment, wherein the portable drinking apparatus comprises a pouch having a liquid reservoir inserted therein and a drinking tube having a first end in fluid communication with the liquid reservoir and a second end having a mouth operated valve. In one embodiment, the compartment is configured to allow two-way air flow so that a discharge of herbal aroma can be released. In another embodiment, the liquid reservoir includes water, electrolytes, glycerol, lactates, and combinations thereof. In still another embodiment, the compartment may include a surface formed from a meshed fabric material, the meshed fabric material configured for direct contact with a wearer's skin.

The therapeutic element may be a herb selected from the group consisting of bergamot, clary sage, cypress, eucalyptus, fennel, geranium, ginger, helichrysum, jasmine, lavender, lemon, lemongrass, mandarin, neroli, patchouli, peppermint, chamomile, rose, rosemary, sandalwood, tea tree, vetiver, ylang-ylang, and combinations thereof. In another embodiment, the therapeutic element may include a combination of a herb and an essential oil. For example, the combination may include a herb selected from the group consisting of rosemary, peppermint, lemongrass, and combinations thereof and an essential oil comprising rosemary oil.

In other embodiments, an apparatus for providing a dual therapy is provided having a garment including a torso portion and a pair of leg portions, wherein the torso portion and the leg portions each include a compartment positioned thereon, the compartment including a therapeutically effective amount of an herb selected from rosemary, peppermint, or lemongrass, and a therapeutically effective amount of an essential oil selected from rosemary oil or peppermint oil, wherein the therapeutically effective amount of the herb is about 0.5 ounces to about 3 ounces, for example, about 1 ounce to about 2.5 ounces, and the therapeutically effective amount of the essential oil is about 5 mL to about 30 mL, for example, about 10 mL to about 25 mL, and a portable drinking apparatus operatively attached to the garment, wherein the portable drinking apparatus includes a liquid reservoir and a drinking tube having a first end in fluid communication with the liquid reservoir and a second end having a mouth operated valve, wherein the liquid reservoir includes water, electrolytes, and combinations thereof.

In one embodiment, the compartment may further include a heat pack or a cold pack. In another embodiment, the garment is a shirt, shorts, pants, bodysuit, or sports bra. In still another embodiment, the compartment is positioned on at least one of the leg portions in an area sufficient for contact with a wearer's thigh. In yet another embodiment, the compartment is positioned on the torso portion in an area sufficient for contact with a wearer's lower back.

In some embodiments, the compartment is configured to allow two-way air flow so that a discharge of herbal aroma can be released. In another embodiment, the compartment is formed from polyvinyl chloride (PVC), polyester, polyethylene terephthalate (PET), polyvinylidene chloride (PVDC), or a meshed fabric material. For example, the compartment may include a surface formed from a meshed fabric material, the meshed fabric material configured for direct contact with a wearer's skin. In still another embodiment, the liquid reservoir is removably attached to the torso portion of the garment. In yet another embodiment, the liquid reservoir is integrally formed with the torso portion of the garment. In still another embodiment, the garment is made from nylon, polyester, spandex, or combinations thereof.

In yet other embodiments, a method for providing aromatherapy and enhancing hydration in a subject in need thereof is provided. In this aspect, the method includes treating the subject by securing the apparatus described above to the subject, wherein the apparatus provides aromatherapeutic effects and enhanced hydration. In one embodiment, the treating step occurs for about two hours to about 16 hours.

BRIEF DESCRIPTION OF THE DRAWINGS

Further features and advantages of the invention can be ascertained from the following detailed description that is provided in connection with the drawings described below.

DETAILED DESCRIPTION OF THE INVENTION

Figure 1:
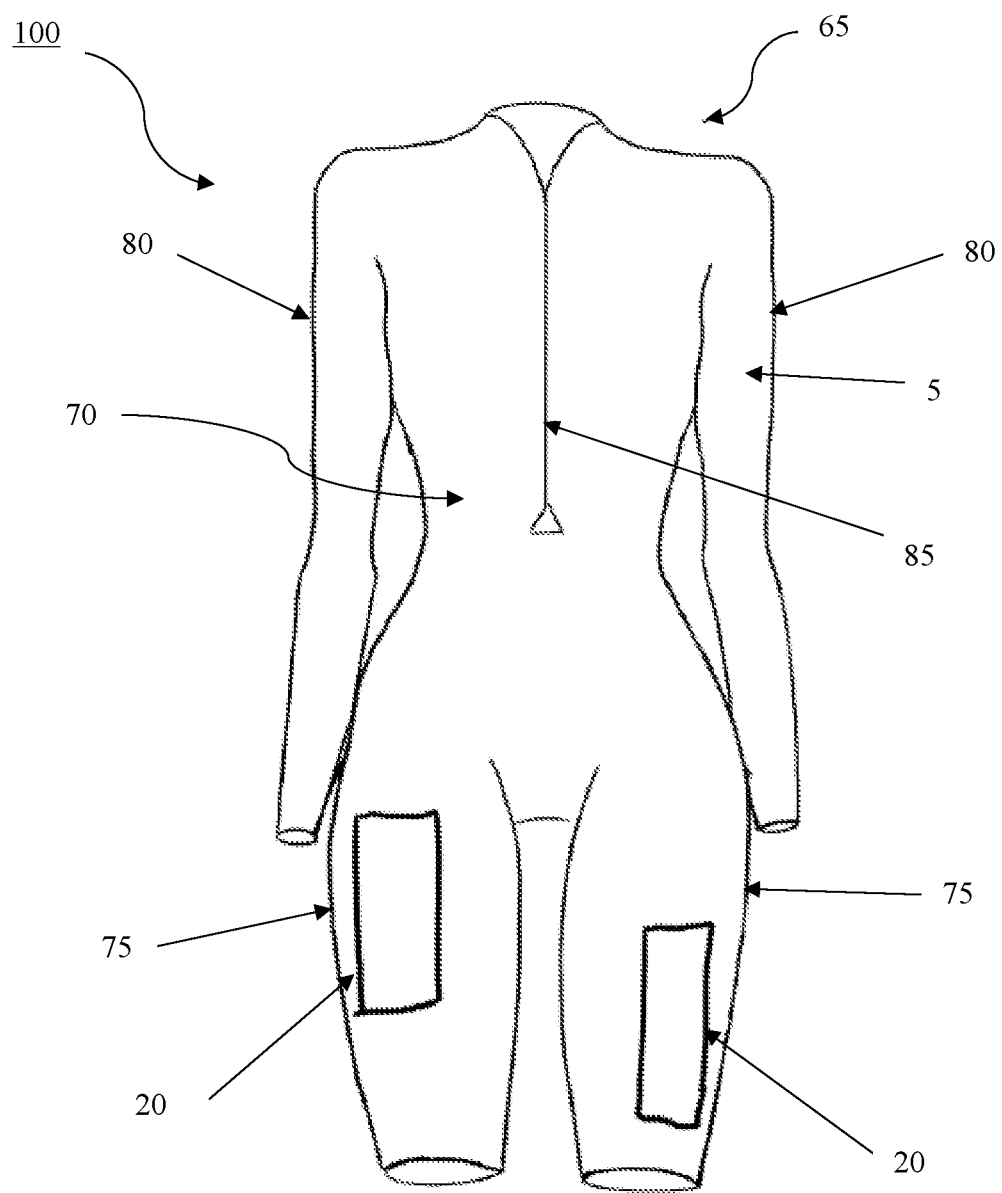
FIG. 1 is a front view of a therapeutic garment according to one embodiment of the present disclosure.

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given in this description are approximate unless stated otherwise, meaning that the term "about" or "approximately" can be inferred when not expressly stated. Numerical quantities in the claims are exact unless stated otherwise.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting. As used herein, the singular forms "a", "an" and "the" are intended to include the plural forms as well, unless the context clearly indicates otherwise.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

In some places reference is made to standard methods, such as but not limited to methods of measurement. It is to be understood that such standards are revised from time to time, and unless explicitly stated otherwise reference to such standard in this disclosure must be interpreted to refer to the most recent published standard as of the time of filing.

The present disclosure discloses an apparatus that provides both aromatherapy and hydration. More particularly, the present disclosure provides garments that include one or more elements, such as herbs or essential oils, that provide therapeutic effects upon inhalation or bodily application. Without being bound by any particular theory, it is believed that placing therapeutic elements in close proximity to body parts of the user that are typically sore or aching can provide numerous benefits including, for instance, managing pain, soothing sore joints, reducing stress, agitation, and anxiety, and improving digestion. The garments may also include a portable source of hydration for the wearer.

Figure 2:
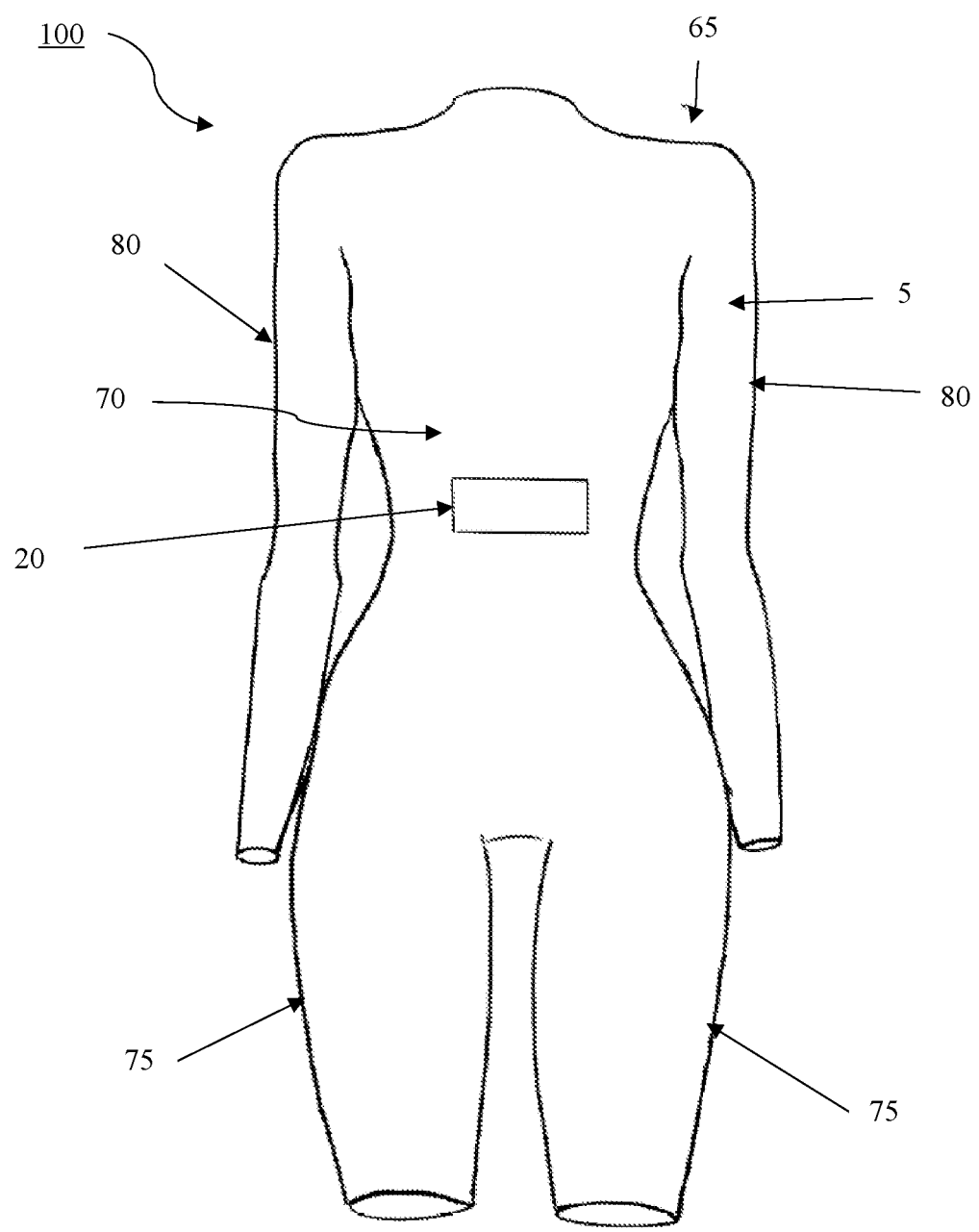
FIG. 2 is a back view of the therapeutic garment of FIG. 1.

Referring to FIGS. 1 and 2, one embodiment of a therapeutic garment 100 according to the present disclosure is described in detail. FIG. 1 is a front view of the therapeutic garment 100 according to one embodiment of the present disclosure, while FIG. 2 shows a back view of the therapeutic garment 100. As shown in FIGS. 1 and 2, the garment 100 contains one or more compartments 20 for inclusion of a therapeutic element (not shown) that can provide any of the benefits described above.

The garment 100 may be any type of article of clothing including, but not limited to, shirts, vests, shorts, pants, bodysuits, skirts, dresses, robes, sports bras, and underwear. As shown in FIGS. 1 and 2, the garment 100 may be a bodysuit. The garment 100 may come in a variety of shapes and sizes to accommodate the body shapes of men, women, and children of all sizes. In one embodiment, the garment 100 is intended to snugly fit the body of the wearer such that the therapeutic element within the compartment 20 is pressed against a body part of the wearer due to the snug fit of the garment 100.

As illustrated in FIGS. 1 and 2, the garment 100 may be a bodysuit having a torso portion 70, a pair of arm portions 80, a pair of leg portions 75 adapted to encircle the wearer's legs, and a closure apparatus 85, such as a zipper, hook and loop fastener, button, or snap. As used herein, "torso" refers to the wearer's chest, back, and abdomen. In one embodiment, the leg portions 75 may terminate at the wearer's thighs. In other embodiments, the leg portions 75 may extend downward to the wearer's ankles. Similarly, the arm portions 80 can be non-existent to form a sleeveless garment 100 or terminate at varying lengths on the arm depending on the wearer's preferences.

The garment 100 may be made from any type of permeable material that allows for two-way air flow and escape of the aroma from the therapeutic element to the user's body. In this aspect, the permeable material should also be thin enough to allow for the two-way air flow. Thicker materials may not allow for the aroma from the therapeutic element to reach the user's body. In one embodiment, the garment 100 may be made from nylon, polyester, spandex, elastane, or combinations thereof. For instance, the garment 100 may be made from spandex. In another embodiment, the garment 100 may be made from a meshed material so as to provide more air pockets for air flow.

As noted above, the compartment 20 holds the therapeutic element. The compartment 20 is a pocket located on the garment 100 in which the therapeutic element is inserted. The compartment 20 should have at least one opening for inserting and removing the therapeutic element. Indeed, the compartment 20 is intended to be reusable such that the therapeutic element can be replaced upon depletion of its therapeutic effects. In one embodiment, the compartment 20 is located on an exterior surface 5 of the garment 100 (as depicted in FIG. 1). An exterior surface 5 of the garment 100 is any surface that faces outwardly away from the wearer. In another embodiment, the compartment 20 may be located on an interior surface (not shown) of the garment 100. An interior surface is any surface that faces inwardly toward the wearer.

The compartment 20 may be positioned at any location on the exterior surface 5 or interior surface of the garment 100. In one embodiment, the compartment 20 is positioned adjacent to a body part of the user that is susceptible to pain or soreness. For instance, as shown in FIG. 1, the compartment 20 may be positioned on each of the leg portions 75 in an area sufficient to contact the wearer's thighs. The compartment 20 may also be positioned on each of the leg portions 75 in an area sufficient to contact the wearer's shins. In another embodiment, the compartment 20 may be positioned on each of the arm portions 80. In still another embodiment, as shown in FIG. 2, the compartment 20 may be positioned on the torso portion 70 in an area sufficient to contact the wearer's lower back. In yet another embodiment, the compartment 20 may be positioned on the torso portion 70 in an area sufficient to contact the wearer's abdomen. In yet another embodiment, the compartment 20 may be positioned on the wrist of the user.

In some embodiments, the compartment 20 is positioned adjacent to and/or in contact with a muscle, tendon, or ligament that is susceptible to pain or soreness. For instance, the compartment 20 may be positioned on the lower back in a horizontal orientation to maximize the surface area of the compartment 20 for contact with the muscles in the lower back, such as the extensor muscles and the erector spinae. In another embodiment, the compartment 20 may be positioned on the lower back in a vertical orientation to maximize the surface area of the compartment 20 for contact with the muscles, tendons, and ligaments in the vertebrae in the lower part of the spine. As another example, the compartment 20 may be positioned on the upper back in a vertical or horizontal orientation to maximize the surface area of the compartment 20 for contact with the muscles in the upper back and shoulders, such as the levator scapulae, trapezius, and deltoid. In still other embodiments, the compartment 20 may be positioned on the legs in a vertical orientation to maximize the surface area of the compartment 20 for contact with the muscles in the thighs, such as the gluteal muscles and the quadriceps femoris muscles, and the muscles in the calves, such as the gastrocnemius muscle.

In one embodiment, the compartment 20 is securely attached to the exterior surface 5 or interior surface of the garment 100. The compartment 20 may be securely attached to the garment 100 by any known means, including, but not limited to, by sewing, bonding, stitching, thermally activated adhesives or polymers, standard glues or adhesives, melting/fusion of polymers or other materials together, mechanical fasteners, and the like. In another embodiment, the compartment 20 is removably and/or adjustably secured to the exterior surface 5 or interior surface of the garment 100. In this aspect, the compartment 20 may be removably and/or adjustably secured by any removable means including, but not limited to, snap and catch elements, hook and loop fasteners, zippers, snaps, and the like.

The compartment 20 may be made from any air permeable, durable material that allows for the escape of aroma therapy to the surrounding environment, while also preventing the therapeutic elements from spilling or leaking from the compartment 20. In one embodiment, the compartment 20 is made from plastic such as polyvinyl chloride (PVC), polyester, polyethylene terephthalate (PET), and polyvinylidene chloride (PVDC). In another embodiment, the compartment 20 is made from a meshed material.

In some embodiments, the compartment 20 may have at least one surface made from a meshed material. Suitable meshed materials include those that are semi-permeable to air flow and contain a sufficient number of apertures for allowing air and liquids to pass therethrough. The meshed material advantageously allows for the contents of the compartment 20, such as therapeutic elements, to directly contact the skin of the wearer. In some embodiments, the surface of the compartment 20 having the meshed material is configured for contact with the skin of the user. In this embodiment, when the compartment 20 is attached to the exterior of the garment 100, the garment 100 may include a cutout complementary in shape to the compartment 20 such that the surface made from the meshed material has direct contact with the skin of the wearer. Similarly, when the compartment 20 is attached to the interior of the garment 100, the compartment 20 should be attached such that the surface made from the meshed material is in direct contact with the skin of the wearer.

In the illustrated embodiments, the compartments 20 are rectangularly shaped. However, the compartments 20 may be any shape that allows for the secure placement of the therapeutic elements on the garment 100, such as circular, triangular, oval, or diamond shaped. The compartments 20 may also be any size so long as the compartment 20 is sufficiently sized to fit the therapeutic element. The wearer may also desire varying sizes of the compartment 20 depending on the body part in which the compartment 20 is intended to contact.

As described above, the garment 100 contains one or more compartments 20 for inclusion of the therapeutic element. The compartment 20 may include any type of therapeutic element that provides therapeutic effects upon inhalation or bodily application. In one embodiment, the therapeutic element is a herbal remedy. Suitable herbs include, but are not limited to, bergamot, clary sage, cypress, eucalyptus, fennel, geranium, ginger, helichrysum, jasmine, lavender, lemon, lemongrass, mandarin, neroli, patchouli, peppermint, chamomile, rose, rosemary, sandalwood, spearmint, tea tree, vetiver, ylang-ylang, and combinations thereof. In one embodiment, the therapeutic element is rosemary. Rosemary is a rich source of antioxidants and anti-inflammatory compounds that have been shown to boost the immune system, improve blood circulation, reduce joint inflammation, and enhance memory and concentration. In another embodiment, the therapeutic element is peppermint. Peppermint has advantageously been shown to soothe an upset stomach, boost energy, relieve migraine headaches and menstrual cramps, reduce spasms and muscle pains, and promote healthy breathing during exercise. In still another embodiment, the therapeutic element is lemongrass. Lemongrass contains substances that are believed to relieve pain and swelling, reduce fever, improve levels of sugar and cholesterol in blood, and reduce excessive sweating and anxiety. In yet another embodiment, the therapeutic element is lavender. In still another embodiment, the therapeutic element is spearmint.

In another embodiment, the therapeutic element is an essential oil. Any of the herbs described above may be used in the form of an essential oil. For instance, suitable essential oils include, but are not limited to, lavender oil, tea tree oil, peppermint oil, lemon oil, rose oil, rosemary oil, chamomile oil, jasmine oil, and ylang-ylang oil. In still another embodiment, the therapeutic element may include a combination of one or more herbs and one or more essential oils. For example, the therapeutic element may include one or more herbs in combination with rosemary oil. In one embodiment, the therapeutic element may include a combination of lemongrass and rosemary oil.

The disclosed therapeutic elements may be used in a therapeutically effective amount so as to be effective in the treatment and prevention of the symptoms discussed herein. The terms "therapeutically effective amount" and "effective amount" refer to a dosage sufficient to treat, inhibit, prevent, reduce the severity of, or alleviate one or more symptoms or to otherwise provide a desired pharmacologic and/or physiologic effect. In one embodiment, the disclosed therapeutic elements may be used in a therapeutically effective amount so as to be effective in the treatment and prevention of one or more of the following symptoms: boost the immune system, improve blood circulation, reduce joint inflammation, enhance memory and concentration, soothe an upset stomach, boost energy, relieve migraine headaches, relieve menstrual cramps, reduce spasms and muscle pains, promote healthy breathing during exercise, relieve pain and swelling, reduce fever, improve levels of sugar and cholesterol in blood, and reduce excessive sweating and anxiety.

The precise amount of therapeutic element to be used may vary according to a variety of factors such as, but not limited to, the wearer's symptoms, weight, sex, and age. Indeed, the selected amount depends upon the desired therapeutic effect and on the duration of the treatment desired. However, in one embodiment, the therapeutic element is used in a therapeutically effective amount of about 0.25 ounces to about 5 ounces. In another embodiment, the therapeutic element is used in a therapeutically effective amount of about 0.5 ounces to about 3 ounces. In still another embodiment, the therapeutic element is used in a therapeutically effective amount of about 1 ounce to about 2.5 ounces. For instance, the therapeutic element may be used in a therapeutically effective amount of about 0.5 ounces to about 1 ounce.

In some embodiments, when the therapeutic element is used in liquid form (for instance, as an essential oil), the therapeutic element may be used in a therapeutically effective amount of about 3 mL to about 30 mL. In another embodiment, when the therapeutic element is used in liquid form (for instance, as an essential oil), the therapeutic element may be used in a therapeutically effective amount of about 5 mL to about 25 mL. In still another embodiment, when the therapeutic element is used in liquid form (for instance, as an essential oil), the therapeutic element may be used in a therapeutically effective amount of about 8 mL to about 20 mL. In yet another embodiment, when the therapeutic element is used in liquid form (for instance, as an essential oil), the therapeutic element may be used in a therapeutically effective amount of about 10 mL to about 15 mL.

As noted above, the therapeutic element can be replaced upon depletion of its therapeutic effects. The duration of the therapeutic effects may vary depending upon the type and amount of the herbs and/or essential oils used. In one embodiment, the effects of the herbal remedy and/or essential oils may last for up to two weeks. In another embodiment, the effects of the herbal remedy and/or essential oils may last for up to about 10 days. In still another embodiment, the effects of the herbal remedy and/or essential oils may last for up to 7 days. In yet another embodiment, the effects of the herbal remedy and/or essential oils may last for up to 5 days.

While the therapeutic elements have been exemplified herein as herbs and/or essential oils, it is to be appreciated that other therapeutic elements may be used in the compartment 20. For example, the therapeutic element may also include a heat pack or a cold (ice) pack of the type commonly used as hot or cold compresses on injured or sore body parts. These elements may be inserted into the compartment 20 and used in combination with the herbs and/or essential oils.

Figure 3:
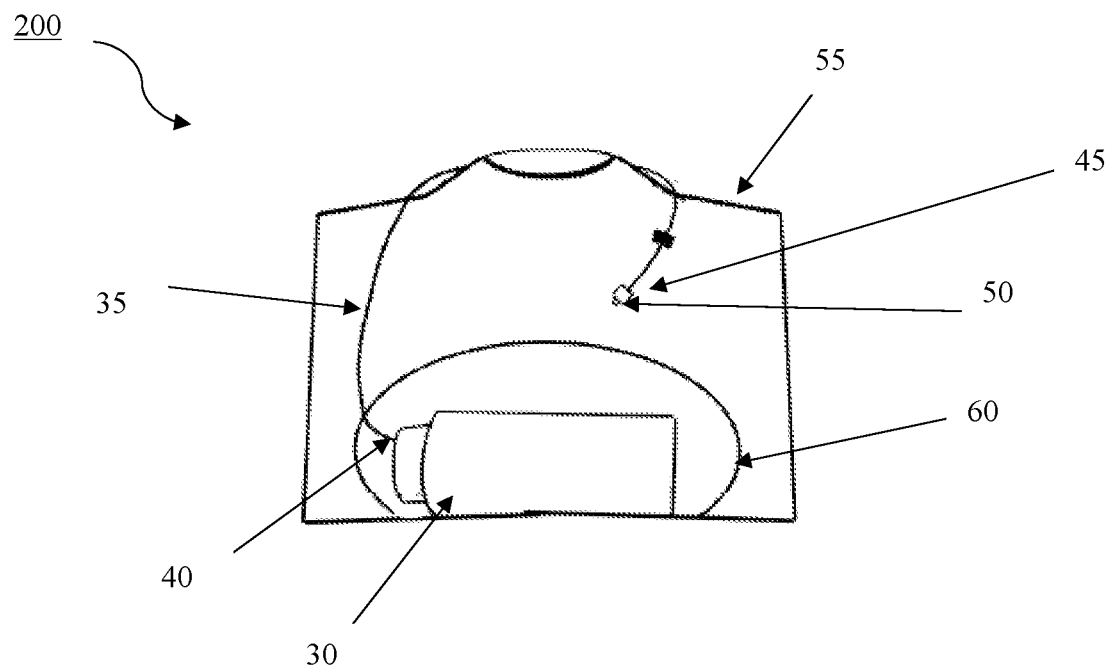
FIG. 3 is a front view of a portable drinking apparatus according to one embodiment of the present disclosure.
Figure 4:
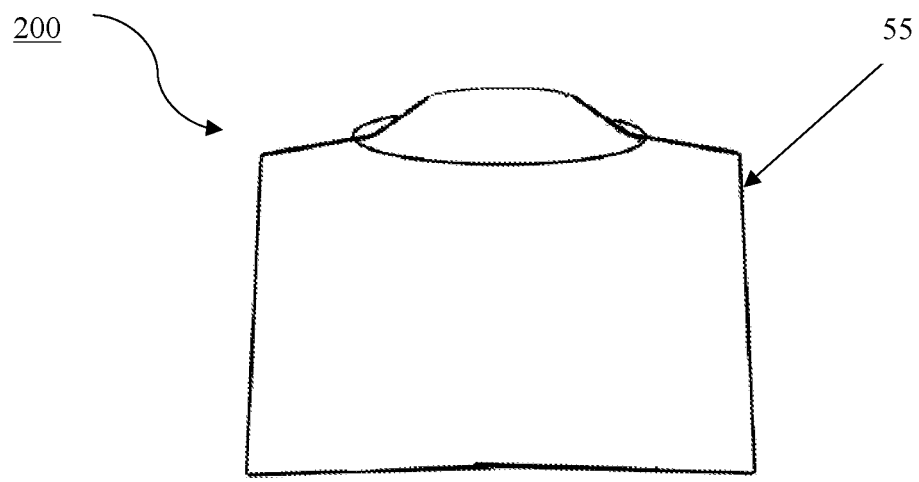
FIG. 4 is a back view of the portable drinking apparatus of FIG. 3.

The present disclosure also provides a portable drinking apparatus that may be worn with the garment 100. Referring to FIGS. 3 and 4, one embodiment of a portable drinking apparatus 200 according to the present disclosure is described in detail. FIG. 3 is a front view of the portable drinking apparatus 200 according to one embodiment of the present disclosure, while FIG. 4 shows a back view of the portable drinking apparatus 200. The portable drinking apparatus 200 provides the wearer with a source of water or other hydrating liquid that can be used for hydration in combination with the therapeutic effects of garment 100. Indeed, the portable drinking apparatus 200 can be used for hydration of humans at rest, during exercise, and after exercise/dehydration.

The portable drinking apparatus 200 includes a liquid reservoir 30 that houses a liquid, such as water, for consumption. The liquid reservoir 30 may be any type of durable container suitable for storing a liquid. In one embodiment, the liquid reservoir 30 is made of polyethylene terephthalate (PET), high-density polyethylene (HDPE), low-density polyethylene (LDPE), or combinations thereof. The liquid reservoir 30 may house any type of hydrating fluid for consumption by the wearer. For instance, the liquid reservoir 30 may include water, glycerol, electrolytes, various lactates, such as sodium lactate, calcium lactate, ferrous lactate, potassium lactate, magnesium lactate, and zinc lactate, and combinations thereof.

The portable drinking apparatus 200 also includes a drinking tube 35 for transporting the liquid from the liquid reservoir 30 to the wearer for consumption. In one embodiment, the drinking tube 35 has a first end 40 that is in fluid communication with the liquid reservoir 30 and a second end 45 that is operably connected to a drinking valve 50. The drinking valve 50 triggers the flow of water from the liquid reservoir 30 through the drinking tube 35 to the wearer by mouth suction. Any type of bite valve known in the art may be used as the drinking valve 50. The drinking valve 50 may be operably connected to the drinking tube 35 by any known adapter, for instance, a female adapter.

In one embodiment, the portable drinking apparatus 200 may be worn with the garment 100. In this embodiment, the liquid reservoir 30 may be attached directly to the garment 100. For example, the liquid reservoir 30 may be integrally formed with the garment 100. In another embodiment, the liquid reservoir 30 may be attached to a piece of fabric that can be worn with the garment 100. For instance, the liquid reservoir 30 may be attached to a cape 55 that can be worn over a shoulder portion 65 of the garment 100. In one embodiment, as shown in FIG. 3, the cape 55 may include a pouch 60 that houses the liquid reservoir 30. The pouch 60 should have at least one opening so that the drinking tube 35 can extend through the pouch 60. The size of the pouch 60 can vary depending on the size of the liquid reservoir 30. As shown in FIG. 3, the pouch 60 and liquid reservoir 30 are located on the front side of the cape 55. However, the pouch 60 and the liquid reservoir 30 may be located anywhere on the cape 55 or garment 100 so long as the drinking tube 35 and drinking valve 50 are accessible to the wearer. In another embodiment, the liquid reservoir 30 may be supported on the cape 55 by any removal securing means, such as by hook and loop fasteners, adhesives, or magnets. In still another embodiment, the pouch 60 itself may house the liquid for consumption. In this embodiment, the pouch 60 can be bonded, for instance, heat bonded, to the cape 55 to provide a watertight seal and prevent leakage.

The cape 55 can be made from any material that is strong enough to support the pouch 60 and the liquid reservoir 30. In one embodiment, the cape 55 is made from neoprene. The pouch 60 can be made from any material that can support the weight of the liquid reservoir 30. In some embodiments, the pouch 60 is made of plastic such as polyvinyl chloride (PVC), polyester, polyethylene terephthalate (PET), and polyvinylidene chloride (PVDC). The pouch 60 can be attached to the cape 55 using any known methods including, but not limited to, by heat binding, sewing, bonding, stitching, thermally activated adhesives or polymers, and the like.

Figure 5:
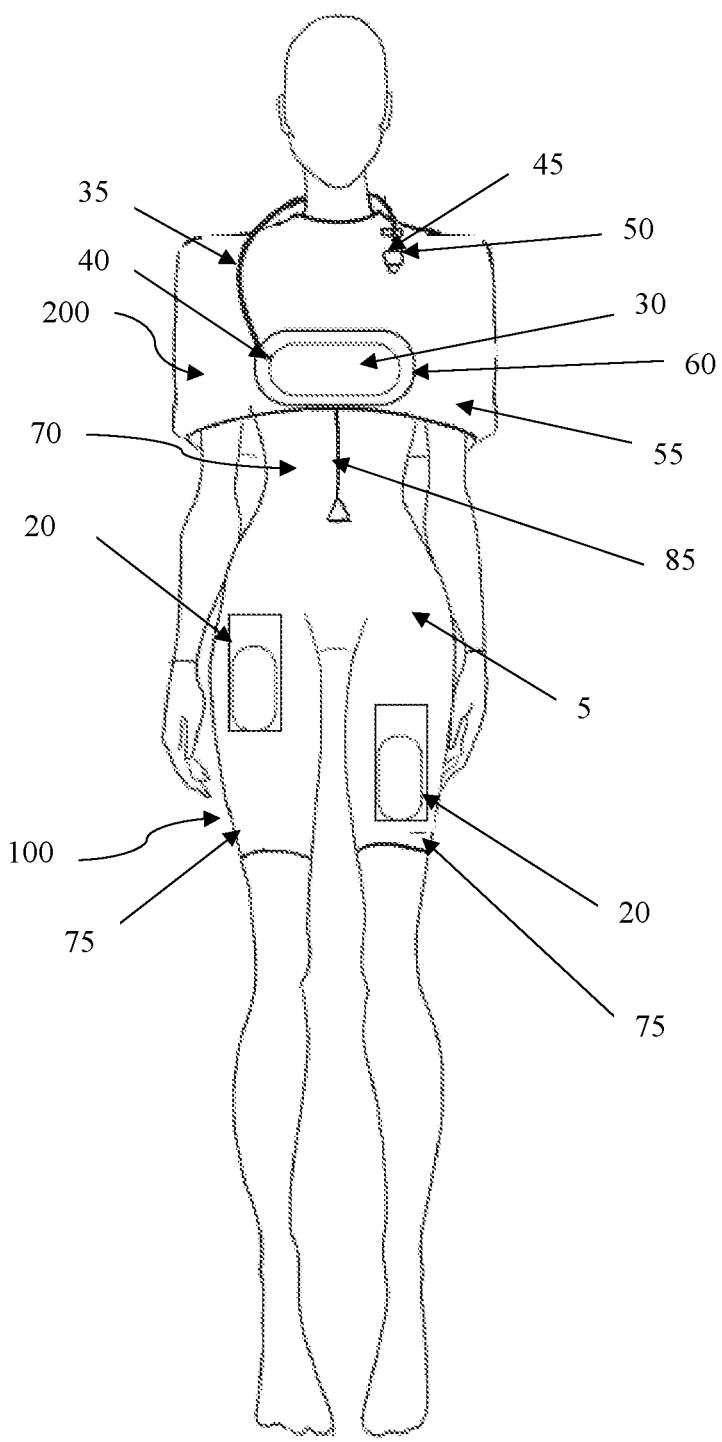
FIG. 5 is a front view of the therapeutic garment having the portable drinking apparatus attached thereto.
Figure 6:
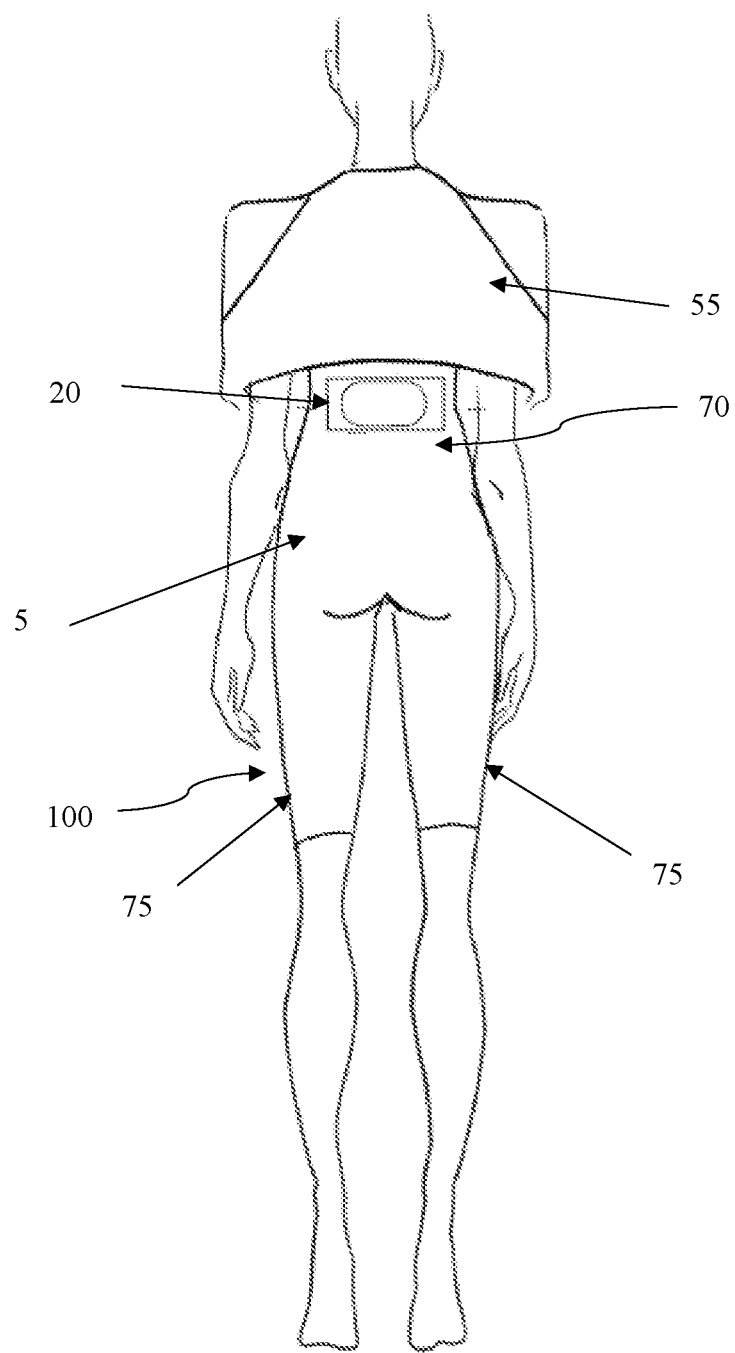
FIG. 6 is a back view of the therapeutic garment having the portable drinking apparatus attached thereto.

FIGS. 5 and 6 show front and back views, respectively, of the therapeutic garment 100 having the portable drinking apparatus 200 attached thereto according to an exemplary embodiment of the present disclosure. As shown in FIGS. 5 and 6, the portable drinking apparatus 200 may be worn with the therapeutic garment 100 to provide for the dual benefits of aromatherapy and hydration. The portable drinking apparatus 200, including the liquid reservoir 30, may be removably attached to the cape 55, which can be placed over the shoulder portion 65 of the garment 100. This allows for easy and convenient access to the portable drinking apparatus 200 for the wearer before, during, and after exercise or other athletic activity.

The present disclosure further provides methods of using the apparatus described above. In one embodiment, a method for providing aromatherapy and enhancing hydration in a subject in need thereof is provided. By using the garment and portable drinking apparatus described above, the method advantageously allows for a subject in need thereof to receive the benefits of the therapeutic elements, for instance, relief of pain, swelling, and joint inflammation, at the same time as receiving the benefits of enhanced hydration. In one embodiment, the subject in need thereof is an athlete. In this aspect, the method can be performed at rest, during the exercise, and/or after the exercise.

According to one embodiment, the method includes providing the garment 100 and/or portable drinking apparatus 200 described above to the subject in need thereof. The subject may wear the garment 100 so that the garment 100 is securely attached to the subject's body. The subject may optionally attach the portable drinking apparatus 200 to the garment 100. As described above, the portable drinking apparatus 200 may be worn as the cape 55 and placed over the shoulders of the subject. In another embodiment, the portable drinking apparatus 200 may be removably attached directly to the garment 100 by any suitable means including, for instance, snap and catch elements, hook and loop fasteners, zippers, snaps, pins, and the like.

The duration of treatment with the garment 100 and/or portable drinking apparatus 200 described herein can vary based on the condition or disorder to be treated. The duration of treatment can extend over several days or longer, depending on the condition, with the treatment continuing until the symptoms of the condition or disorder are sufficiently reduced or eliminated. The progress of this therapy can be monitored by conventional techniques and may be used to adjust the dosage/treatment to achieve a therapeutic effect.

In one embodiment, the duration of treatment is from about one hour to about one day. For instance, the garment 100 and/or portable drinking apparatus 200 can be worn by the subject for about two hours to about 16 hours. In another embodiment, the duration of treatment is from about four hours to about 12 hours. In still another embodiment, the duration of treatment is from about six hours to about 10 hours.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and are capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. An apparatus for providing a dual therapy, comprising:
a garment comprising a torso portion and a pair of leg portions, wherein the torso portion and the leg portions each comprise a compartment positioned thereon, the compartment comprising a therapeutically effective amount of an herb selected from rosemary, peppermint, or lemongrass, and a therapeutically effective amount of an essential oil selected from rosemary oil or peppermint oil,
wherein the therapeutically effective amount of the herb is about 0.5 ounces to about 3 ounces and the therapeutically effective amount of the essential oil is about 5 mL to about 30 mL, and
a portable drinking apparatus operatively attached to the garment, wherein the portable drinking apparatus comprises a liquid reservoir and a drinking tube having a first end in fluid communication with the liquid reservoir and a second end having a mouth operated valve, wherein the liquid reservoir comprises water, electrolytes, and combinations thereof.

2. The apparatus of claim 1, wherein the compartment further comprises a heat pack or a cold pack.

3. The apparatus of claim 1, wherein the compartment is positioned on at least one of the leg portions in an area sufficient for contact with a wearer's thigh.

4. The apparatus of claim 1, wherein the compartment is positioned on the torso portion in an area sufficient for contact with a wearer's lower back.

5. The apparatus of claim 1, wherein the therapeutically effective amount of the herb is about 1 ounce to about 2.5 ounces.

6. The apparatus of claim 1, wherein the therapeutically effective amount of the essential oil is about 10 mL to about 25 mL.

7. The apparatus of claim 1, wherein the compartment is configured to allow two-way air flow so that a discharge of herbal aroma can be released.

8. The apparatus of claim 1, wherein the compartment is formed from polyvinyl chloride (PVC), polyester, polyethylene terephthalate (PET), polyvinylidene chloride (PVDC), or a meshed fabric material.

9. The apparatus of claim 1, wherein the garment is made from nylon, polyester, spandex, or combinations thereof.

10. The apparatus of claim 1, wherein the compartment comprises a surface formed from a meshed fabric material, the meshed fabric material configured for direct contact with a wearer's skin.

11. The apparatus of claim 1, wherein the liquid reservoir is removably attached to the torso portion of the garment.

12. The apparatus of claim 1, wherein the liquid reservoir is integrally formed with the torso portion of the garment.

\* \* \* \* \*